United States Patent [19]

Neubauer et al.

[11] Patent Number: 5,575,797
[45] Date of Patent: Nov. 19, 1996

[54] DEVICE FOR EXPLANTING A MEDICAL ELECTRODE DEVICE

[75] Inventors: Heinz Neubauer, Jaerfaella; Ulf Lindegren, Enskede, both of Sweden; Modesto Guerola, Barcelona, Spain

[73] Assignee: Siemens Elema AB, Solna, Sweden

[21] Appl. No.: 310,875

[22] Filed: Sep. 23, 1994

[30] Foreign Application Priority Data

Sep. 24, 1993 [SE] Sweden .................................. 9303122

[51] Int. Cl.$^6$ .................................................. A61B 17/22
[52] U.S. Cl. ............................................ 606/129; 604/269
[58] Field of Search ............................. 128/784, DIG. 9, 128/785; 606/129, 49; 604/269

[56] References Cited

U.S. PATENT DOCUMENTS

| | | | |
|---|---|---|---|
| 4,253,462 | 3/1981 | Dutcher | 606/129 |
| 4,471,777 | 9/1984 | McCorkle | 606/129 |
| 4,886,065 | 12/1989 | Collins | 606/129 |
| 5,320,621 | 6/1994 | Gordon | 606/129 |

Primary Examiner—Michael A. Brown
Attorney, Agent, or Firm—Hill, Steadman & Simpson

[57] ABSTRACT

A device for explanting an electrode device, particularly an intravascular or intracardiac electrode device having an electrode cable and an electrode head arranged on the cable's distal end, is capable of simply and safely detaching fibrotic matter from the entire surface of the electrode cable and electrode head. The explanting device has a stiff first sleeve, relatively short in relation to the length of the electrode cable, and whose diameter is slightly larger than the external diameter of the electrode cable. One end of the sleeve forms a cutting edge. The first sleeve is connected at its end opposite the cutting edge to a first control body in the form of a stylet with which the first sleeve can be moved along the implanted electrode device. A second sleeve, operable with another stylet, amy additionally be employed, having resilient cutting elements. The second sleeve can be slid over and past the first sleeve, causing its cutting elements to move toward each other for cutting fibrotic tissue around the top of the electrode head.

16 Claims, 1 Drawing Sheet

FIG.1
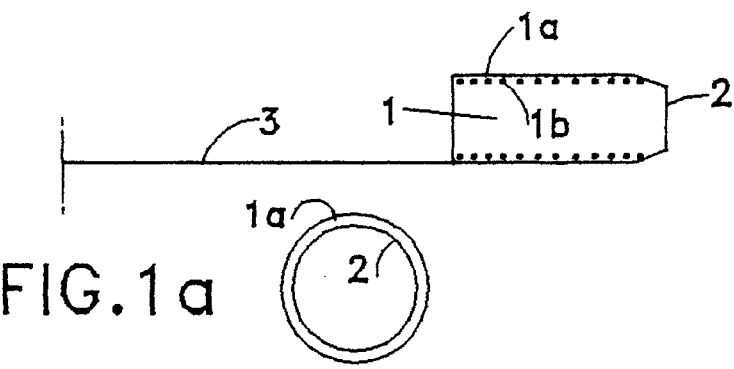
FIG.1a
FIG.2
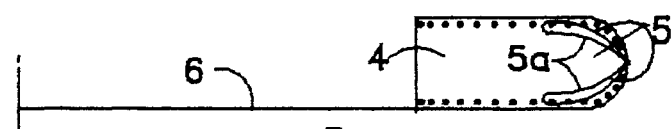
FIG.2a
FIG.3
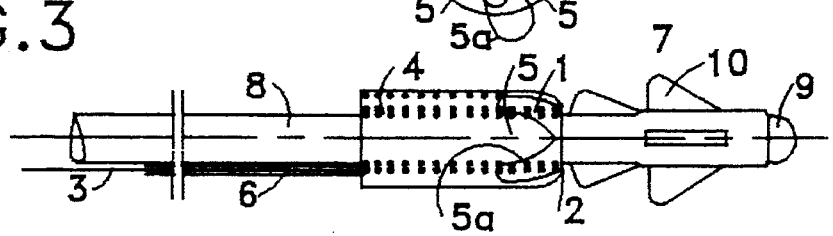
FIG.4
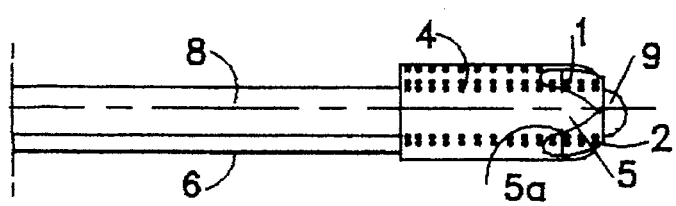
FIG.5
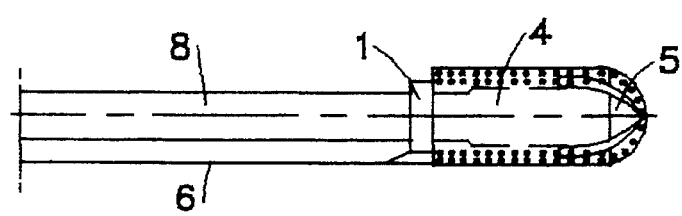

DEVICE FOR EXPLANTING A MEDICAL ELECTRODE DEVICE

BACKGROUND OF THE INVENTION

This invention relates to a device for explanting a medical electrode device, particularly an intravascular or intracardiac electrode device, of the type having an electrode cable and an electrode head arranged at the distal end of the cable.

DESCRIPTION OF THE PRIOR ART

After a time, a permanently implanted device in a patient, such as a pacemaker electrode, becomes coated with connective tissue which anchors the electrode cable so firmly that withdrawing the cable by pulling on the cable's exposed proximal end could be very difficult and even dangerous, since healthy tissue in the area in and around the anchoring site in the heart could be torn out or damaged in some other way. The term "anchoring site" generally refers to the position of the electrode cable's electrode head but can also include fixing devices, such a fins or tines, arranged immediately behind the electrode head, which become coated with connective tissue after only a relatively short period of time. The electrode cable itself may also be attached by fibrotic tissue to the surrounding venous wall. If replacement of the electrode becomes necessary, the physician thus often decides to leave the existing electrode in place and to implant another. In certain instances, e.g. when a plurality of disused, severed electrode cables are situated in the heart via a vein, or if an infection develops, or one of the electrode cables threatens to penetrate a vein or the heart wall, one or more of the electrode cables must unavoidably be removed, either by surgery or by the use of an explantation device.

From published PCT application WO91/19532, and U.S. Pat. No. 4,574,800, explantation devices of the above-mentioned kind are known. All of these known devices consist of stylet-like bodies whose distal ends are either equipped with backwardly projecting tines or radially expandable elements. All the bodies can be introduced through a channel, intended for a stylet, in the electrode device. When the stylet-like body has been inserted so its distal end is immediately behind the electrode head, the tines or elements are made to expand radially so they press against the inner wall of the channel. When explanting the electrode device, the physician must pull on the body which, as noted above, could damage healthy tissue at and around the sites to which the electrode cable is adherent.

Another explantation device of the above-mentioned kind is known from an article entitled "Chronic Transvenous Pacemaker Lead Removal Using a Unique, Sequential Transvenous System" in The American Journal of Cardiology, volume 66, Oct. 15, 1990, pp 964–966. This device consists of two flexible tubes, one tube of which is pushed onto the other so they jointly form a telescoping catheter. The catheter can be slid along the electrode cable and therefore can cut the electrode cable loose from the venous wall. The diameter of the catheter is only slightly larger than the electrode cable's external diameter, resulting in very high friction between cable and catheter. This means, in turn, that sliding this long catheter along the possibly somewhat longer cable cannot be accomplished without difficulties. In addition, the telescoping catheter, which must retain its slidability over a long distance, must have relatively thick walls, so it cannot be very flexible. Moreover, this known device is incapable of detaching the top of the electrode head.

SUMMARY OF THE INVENTION

An object of the present invention is to provide a device for explanting an electrode device of the above-described type which is capable of simply and safely detaching adherent fibrotic matter from the entire surface of the electrode cable and electrode head.

The above object is achieved in accordance with the principles of the present invention in a device which has a stiff first sleeve, which is relatively short in relation tot he length of the electrode cable, whose diameter is somewhat larger than the external diameter of the electrode cable. One end side of the sleeve forms a cutting edge. The sleeve is connected at its end opposite the cutting edge to a first control body in the form of a stylet with which the sleeve can be slid along the implanted electrode device. After the proximal end of the implanted electrode device has been detached from the pacemaker unit, this end is cut off so the sleeve can be slid onto the electrode cable. Since the cable is accessible to the physician, in contrast to an explantation device in the form of a catheter, he or she can easily pull on the proximal end of the cable, thereby straightening out the cable and the vein. Since the sleeve is relatively short and the cable relatively straight, the sleeve, with the aid of the stylet, can be easily slid along the electrode cable, the sleeve's cutting edge slicing off any fibrotic tissue, such as tissue attaching the cable to, e.g., the inner wall of a vein or to the heart wall. The cutting edge on the sleeve can also cut off any projecting fixing devices made of plastic material.

In a further version of the invention, a second sleeve is used, the second sleeve being slidable onto the first sleeve, one end side of this second sleeve being provided with radially resilient, curved cutting elements which, in a first position, press against the outer wall of the first sleeve and, in a second position, press toward each other. The second sleeve is connected at the end opposite the cutting elements to a second control device with which the second sleeve can be slid along the first sleeve so the cutting elements can be moved from the first position to the second position. With this arrangement, even the top of the electrode head can be cut loose from fibrotic tissue when the second sleeve is moved from a first position to a second position, causing the cutting elements to move toward each other. Prior to this, the first sleeve and the second sleeve have been slid down to the distal end of the electrode cable.

At least one sleeve is made of metal. As a result, the cutting edge of the first sleeve and the cutting element son the second sleeve can be made very sharp.

DESCRIPTION OF THE DRAWINGS

FIG. 1 is a side view of a first sleeve according to the invention.

FIG. 2 is a side view and FIG. 2a is an end view, of a second sleeve according to the invention.

FIG. 3 is a side view of the first sleeve and the second sleeve according to FIGS. 1 and 2, the second sleeve being slid onto the first sleeve, and the sleeves additionally being arranged on an electrode cable.

FIGS. 4 and 5 are views of the sleeves according to FIG. 3 in different relative positions and in different positions on the electrode cable.

DETAILED DESCRIPTION OF THE PREFERRED EMBODIMENTS

FIG. 1 shows a device for explanting an electrode device (not shown), particularly an intravascular or intracardiac electrode device. The explanting device has a stiff first sleeve 1, which is relatively short in relation to the length of the electrode cable, and having a tubular channel 1b whose inner diameter is somewhat larger than the external diameter of the electrode cable. One end of the exterior 1a of the sleeve 1 is bevelled and forms an annular cutting edge 2 (shown in an end view in FIG. 1a, as seen from the right of FIG. 1, looking toward the left). The sleeve 1 is also connected at its end opposite the cutting edge 2 to a stylet 3, which is preferably made of stainless steel.

FIG. 2 shows a second sleeve 4, whose length is approximately the same as the length of the first sleeve 1, one end of the second sleeve 4 being provided with resilient, curved cutting elements 5, described below, evenly distributed around the circumference of the sleeve 4. These cutting elements 5 have slight spacings therebetween in the position shown in FIG. 2, and in an end view 2a as seen from the right of FIG. 2 looking toward the left, and the edges 5a of the cutting elements 5 defining these spacings are sharp. The cutting elements 5 are inherently biased, such as by a domed shaping of the distal end of the sleeve 4, so as to be urged toward each other. The sleeve 4 is also provided, on the end opposite the cutting elements 5, with a control device in the form of a relatively thin tube 6 (shown in an exterior view in FIGS. 2, 4 and 5 and schematically in section in FIG. 3).

The diameter of the sleeve 4 is such that the sleeve can be slid onto and along the first sleeve 1, as shown in FIG. 3. In this position, the ends of the cutting elements 5 are forced apart by pressing against the bevelled section of the first sleeve 1. In this way, the curved cutting means 5 do not protrude from the sleeve 4. This is an advantage, since the external diameter of the explantation device should be as small as possible. FIG. 3 also shows that when the second sleeve 4 has been slid onto the first sleeve 1, and the stylet 3 is arranged in the tube 4. FIG. 3 also shows that the stylet 3 for the first sleeve 1 is longer than the tube 6 for the second sleeve 4.

In the explantation of an intracardiac electrode device 7, consisting of the electrode cable 8 and an electrode head 9 on the distal end of the electrode cable 8, whose proximal end is exposed, the electrical contact and sealing part of the electrode cable 8 is usually cut off, since the external diameter of this proximal part is larger than the diameter of the electrode cable 8. The sleeves 1 and 4 are then slid onto the electrode cable 8. The physician can then pull on the proximal end of the electrode cable 8, straightening out the cable as well as the vein in which it is situated. The sleeves 1 and 4, with the aid of the stylet 3, can then be slid along the electrode cable 8, and the cutting edge 2 of the sleeve 1 can cut off any connective tissue from the surface of the electrode cable 8. In FIG. 3, the sleeves 1 and 4 are shown in a position in which they have been advanced to fin-like fixing elements 10 arranged immediately behind the electrode head 8 and made of a plastic material. Fixing elements 10 of the illustrated kind usually become coated with fibrotic tissue and are usually very firmly anchored in the cardiac trabeculae. The physician can, by sliding the sleeves 1 and 4, cut off this tissue from the surface of the electrode cable 8 using the cutting edge 2.

In FIG. 4, the sleeves 1 and 4 are shown in a position in which they have been advanced to a point immediately behind the electrode head 9, thereby resulting in detachment of fibrotic tissue from the entire electrode cable 8. When the tube 6 is moved forward from this position in relation to the stylet 3, the second sleeve 4 moves in relation to the first sleeve 1, causing the cutting elements 5 to move toward and against each other, thereby freeing top of the electrode head 9 from fibrotic tissue. One such position is shown in FIG. 5. The entire device is now free from fibrotic tissue and can be withdrawn from the patient's heart and veins. Since the sleeves can advantageously be made of metal, the cutting edge 2 and the cutting elements 5 can be made very sharp.

The stylet 3 for the first sleeve 1 need not necessarily be inserted into the tube 6 for the second sleeve 4; they can be separate.

A very simple explantation device is also achieved even if only the first sleeve 1 is used in the described way for detaching the cable 8 from tissue, e.g. when the physician is convinced, for one reason or another, that the top of the electrode head 9 is not firmly adherent to fibrotic tissue in the heart wall.

Although the present invention has been described with reference to a specific embodiment, those of skill in the art will recognize that changes may be made thereto without departing from the scope and spirit of the invention as set forth in the appended claims.

We claim as my invention:

1. An explanting device for explanting an implanted electrode device, said electrode device comprising an intravascular or intracardiac electrode device having an electrode cable with a length, a diameter and a distal end, and an electrode head disposed at said distal end, said explanting device comprising:

a stiff sleeve having a length which is substantially shorter than the length of said electrode cable and a diameter which is slightly larger than said diameter of said electrode cable;

an annular cutting edge disposed at one end of said sleeve facing said distal end of said cable; and control means, manipulatable by a user, connected at an end of said sleeve opposite said cutting edge for sliding said sleeve along an exterior of said implanted electrode device to cut fibrotic tissue.

2. An explanting device as claimed in claim 1, wherein said control means comprises a stylet.

3. An explanting device as claimed in claim 2, wherein said stylet consists of stainless steel.

4. An explanting device as claimed in claim 1, wherein said sleeve consists of metal.

5. An explanting device as claimed in claim 1, wherein said sleeve comprises a first sleeve and wherein said control means comprise first control means, and said explanting device further comprising:

a second sleeve slidable over said first sleeve, said second sleeve having a plurality of cutting elements disposed at an end of said second sleeve facing said distal end of said electrode cable, said cutting elements being resilient and biased to press toward said electrode cable but being forced away from said electrode cable by said first sleeve inside said second sleeve; and second control means connected to said second sleeve at a side opposite said cutting elements and manipulatable by said user for moving said second sleeve over said first sleeve toward said distal end of said electrode cable causing said cutting elements to move toward each other for cutting fibrotic tissue surrounding said electrode head.

6. An explanting device as claimed in claim 5, wherein said cutting elements are evenly distributed around a circumference of said second sleeve.

7. An explanting device as claimed in claim 5, wherein said second control means comprises a tube.

8. An explanting device as claimed in claim 5, wherein said second sleeve consists of metal.

9. An explanting device as claimed in claim 5, wherein each of said first and said second sleeve consist of metal.

10. An explanting device as claimed in claim 1, wherein said cutting elements comprise, in combination a dome and wherein said cutting elements are separated by radially proceeding spaces, said cutting elements having cutting edges surrounding said spaces.

11. An explanting device for explanting an implanted electrode device, said electrode device comprising an intravascular or intracardiac electrode device having an electrode cable with a length, a diameter and a distal end, and an electrode head disposed at said distal end, said explanting device comprising:

a stiff first sleeve having a length substantially shorter than the length of said electrode cable and having an inner diameter slightly larger than said diameter of said electrode cable, and having an outer diameter, said first sleeve having an annular cutting edge disposed at an end thereof facing said distal end of said electrode cable;

a second sleeve having a length substantially corresponding to the length of said first sleeve and having an inner diameter slightly larger than said outer diameter of said first sleeve so that said second sleeve is slidable over said first sleeve, said first sleeve having a plurality of resilient cutting elements disposed at an end thereof facing said distal end of said electrode cable, said cutting elements being biased to move toward each other but being forced apart while said second sleeve is on said first sleeve; and control means, manipulatable by a user, for sliding said first sleeve with said second sleeve thereon along said length of said electrode cable for causing said cutting edge of said first sleeve to cut fibrotic tissue surrounding said electrode cable and for, when said first and second sleeves reach said distal end of said cable, moving said second sleeve further toward said distal end so that said cutting elements project beyond said first sleeve and are urged toward to each other for cutting fibrotic tissue surrounding said electrode head.

12. An explanting device as claimed in claim 11, wherein said control means comprise a stylet connected to said first sleeve and a tube connected to said second sleeve.

13. An explanting device as claimed in claim 11, wherein each of said first sleeve and said second sleeve consist of metal.

14. An explanting device as claimed in claim 11, wherein said cutting elements comprise, in combination a dome and wherein said cutting elements are separated by radially proceeding spaces, said cutting elements having cutting edges surrounding said spaces.

15. A method for explanting an implanted electrode device, said electrode device including an electrode cable having a length and a diameter and a distal end and an electrode head disposed at said distal end, said method comprising the steps of:

providing a stiff sleeve with an annular cutting edge at one end thereof; and sliding said sleeve along said length of said implanted electrode cable with said cutting edge facing said distal end of said cable and manipulating sliding of said sleeve from a proximal end of said cable for cutting fibrotic tissue surrounding said length of said cable.

16. A method as claimed in claim 15 comprising the additional steps of:

providing a further sleeve with a plurality of resilient cutting elements at one end thereof, said cutting elements being biased to move toward each other;

placing said further sleeve over said sleeve before sliding said sleeve along said cable, and thereby forcing said cutting elements apart;

sliding said further sleeve together with said first sleeve along said length of said cable while said first sleeve cuts said fibrotic tissue, until reaching said distal end of said electrode cable; and moving said further sleeve beyond said first sleeve at said distal end so that said cutting elements project beyond said first sleeve and move together for cutting fibrotic tissue surrounding said electrode head.

* * * * *